(12) United States Patent
Hillman et al.

(10) Patent No.: US 6,277,373 B1
(45) Date of Patent: Aug. 21, 2001

(54) PHOSPHATIDYLINOSITOL 4,5-BISPHOSPHATE 5-PHOSPHATASE

(75) Inventors: Jennifer L. Hillman, Mountain View; Preeti Lal, Sunnyvale; Neil C. Corley, Mountain View; Purvi Shah, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/258,643

(22) Filed: Feb. 26, 1999

Related U.S. Application Data

(62) Division of application No. 08/884,681, filed on Jun. 27, 1997, now Pat. No. 5,955,338.

(51) Int. Cl.[7] .............................. A61K 38/48; C12N 9/16; C12N 1/20; C12N 15/00; C07H 21/04
(52) U.S. Cl. .................. 424/94.64; 435/196; 435/252.3; 435/320.1; 536/23.2; 530/350; 530/300
(58) Field of Search ........................ 424/94.64; 435/196, 435/252.3, 320.1; 536/23.2; 530/350, 300

(56) References Cited

U.S. PATENT DOCUMENTS 5,716,806 * 2/1998 Meissner et al. .................... 435/69.1

FOREIGN PATENT DOCUMENTS

WO 95/14772   1/1995  (WO) .

OTHER PUBLICATIONS

Rath Hope, H.M. et al., Purification and characterization of a polyphosphoinositide phosphatase from rat brain. *J.Biol.Chem.* (1994) 269:23648–23654.

Jefferson, A.B. et al., Properties of Type II Inositol Polyphosphate 5–Phosphatase. *J.Biol.Chem.* (1995) 270:9370–9377. (GI 1019103).

Nussbaum, R.L., (GI 1399104), GenBank Sequence Database (Accession U45975), National Center for Biotechnology Information, National Library of Medicine, Bethesda, Maryland, 20894.

Nussbaum, R.L. et al., (GI 1420919), GenBank Sequence Database (Accession U57627), National Center for Biotechnology Information, National Library of Medicine, Bethesda, Maryland, 20894. (GI 1420920).

Matzaris, M. et al., Identification and characterization of the phosphatidylinositol–(4,5)–bisphosphate 5–phosphatase in human platelets. *J.Biol.Chem.* (1994) 269:3397–3402.

Nussbaum, et al., Human phosphatidylinositol (4,5) bisphosphate 5–phosphatase homolog mRNA, partial cds., EST Accession No. U45973, release date Jul. 1. 1996.

* cited by examiner

*Primary Examiner*—Ponnathapu Achutamurthy
*Assistant Examiner*—Tekchand Saidha
(74) *Attorney, Agent, or Firm*—Incyte Genomics, Inc.

(57) ABSTRACT

The invention provides a human phosphatidylinositol 4,5-bisphosphate 5-phosphatase (PBPP) and polynucleotides which identify and encode PBPP. The invention also provides expression vectors, host cells, agonists, antibodies and antagonists. The invention also provides methods for treating disorders associated with expression of PBPP.

5 Claims, 15 Drawing Sheets

```
                 9              18          27          36          45          54
5' NNG AAG GCT CAG CAT ACA CGT CGT GAC TTG GAA CGT GGC TTC GGC AGC GCC CCT 63              72          81          90          99         108
   CGA GCT CTC AGT GAC CTG CTT CAG AAC AAC CGG AAC CTC AAT CTT GAC ATA 117             126         135         144         153         162
   TAT GTT ATT GGT TTG CAG GAA TTG AAC TCT GGG ATC ATA AGC CTC CTT TCC GAT 171             180         189         198         207         216
   GCT GCC TTT AAT GAC TCG TGG AGC AGT TTC CTC ATG GAT GTG CTT TCC CCT CTG
                                                M   D   V   L   S   P   L 225             234         243         252         261         270
   AGC TTC ATC AAG GTC TCC CAT GTC CGT ATG CAG GGG ATC CTC TTA CTG GTC TTT
    S   F   I   K   V   S   H   V   R   M   Q   G   I   L   L   L   V   F 279             288         297         306         315         324
   GCC AAG TAT CAG CAT TTG CCC TAT ATC CAG ATT CTG TCT ACT AAA TCC ACC CCC
    A   K   Y   Q   H   L   P   Y   I   Q   I   L   S   T   K   S   T   P 333             342         351         360         369         378
   ACT GGC CTG TTT GGG TAC TGG GGG AAC AAA GGT GGA GTC AAC ATC TGC CTG AAG
    T   G   L   F   G   Y   W   G   N   K   G   G   V   N   I   C   L   K

FIGURE 1A
```

```
     387      396      405      414      423      432
CTT TAT GGC TAT GTC AGC ATC AAC TGC CAC CTG CCT CCC CAC ATT TCC
 L   Y   G   Y   V   S   I   N   C   H   L   P   P   H   I   S 441      450      459      468      477      486
AAC AAT TAC CAG CGG CTG GAG CAC TTT GAC CGG ATC CTG GAG ATG CAG AAT TGT
 N   N   Y   Q   R   L   E   H   F   D   R   I   L   E   M   Q   N   C 495      504      513      522      531      540
GAG GGG CGA GAC ATC CCA AAC ATC CTG GAC CAC GAC CTC ATT ATC TGG TTT GGA
 E   G   R   D   I   P   N   I   L   D   H   D   L   I   I   W   F   G 549      558      567      576      585      594
GAC ATG CGG AAC TTT CGG ATC GAG GAC TGG GAG AAG GAC CAG CTC TTT GTT CGG GAA TCC ATT
 D   M   R   N   F   R   I   E   D   W   E   K   D   Q   L   F   V   R   E   S   I 603      612      621      630      639      648
AAA AAT CGG TGC TAC GGT GGC CTG TGG GAG GAG AAG GAC CAG CTC AGC ATT GCC AAG
 K   N   R   C   Y   G   G   L   W   E   E   K   D   Q   L   S   I   A   K 657      666      675      684      693      702
AAA CAT GAC CCG CTG CTC CGG GAG TTC CAG GAG GGC CGC CTA CTC TTC CCG CCC
 K   H   D   P   L   L   R   E   F   Q   E   G   R   L   L   F   P   P 711      720      729      738      747      756
```

FIGURE 1B

```
ACC TAC AAG TTT GAT AGG AAC TCC AAC GAC TAT GAC ACC AGT GAG AAA AAA CGC
 T   Y   K   F   D   R   N   S   N   D   Y   D   T   S   E   K   K   R
                        765                 774                 783                 792                 801                 810
AAG CCT GCA TGG ACC GAT CGC ATC CTG TGG AGG CTG AAG CGG CAG CCC TGT GCT
 K   P   A   W   T   D   R   I   L   W   R   L   K   R   Q   P   C   A
                        819                 828                 837                 846                 855                 864
GGC CCC GAC ACT CCC ATA CCG CCG TCA CAC TTC TCC TTG TCT CTG AGG GGC
 G   P   D   T   P   I   P   P   A   S   H   F   S   L   S   L   R   G
                        873                 882                 891                 900                 909                 918
TAC AGC CAC ATG ACG TAC GGC ATC AGC GAC CAC AAG CCT GTC TCC GGC ACG
 Y   S   H   M   T   Y   G   I   S   D   H   K   P   V   S   G   T
                        927                 936                 945                 954                 963                 972
TTC GAC TTG GAG CTG AAG CCA TTG GTG TCT GCT CCG CTG ATC GTC CTG ATG CCC
 F   D   L   E   L   K   P   L   V   S   A   P   L   I   V   L   M   P
                        981                 990                 999                 1008                1017                1026
GAG GAC CTG TGG ACC GTG GAA AAT GAC ATG ATG GTC AGC TAC TCT TCA ACC TCG
 E   D   L   W   T   V   E   N   D   M   M   V   S   Y   S   S   T   S
                        1035                1044                1053                1062                1071                1080
```

FIGURE 1C

```
GAC TTC CCC AGC AGC CCG TGG GAC TGG ATT GGA CTG TAC AAG GTG GGG CTG CGG
 D   F   P   S   S   P   W   D   W   I   G   L   Y   K   V   G   L   R
            1089          1098          1107          1116          1125          1134
GAC GTT AAT GAC TAC GTG TCC TAT GCC TGG GTC GGG GAC AGC AAG GTC TCC TGC
 D   V   N   D   Y   V   S   Y   A   W   V   G   D   S   K   V   S   C
            1143          1152          1161          1170          1179          1188
AGC GAC AAC CTG AAC CAG GTT TAC ATC GAC ATC AGC AAT ATC CCT ACC ACT GAA
 S   D   N   L   N   Q   V   Y   I   D   I   S   N   I   P   T   T   E
            1197          1206          1215          1224          1233          1242
GAT GAG TTT CTC CTC TGT TAC TAC AGC AAC AGT CTG CGT TCT GTG GTG GGG ATA
 D   E   F   L   L   C   Y   Y   S   N   S   L   R   S   V   V   G   I
            1251          1260          1269          1278          1287          1296
AGC AGA CCC TTC CAG ATC TGA GCC AGG ATG GGA GTG AAT CCC AGG CGG AGG CCA CTG GGT GAA
 S   R   P   F   Q   I   *
            1305          1314          1323          1332          1341          1350
GCA CAG CCA CAG ATC TGA GCC AGG ATG GGA GTG AAT CCC AGG CGG AGG CCA GAG
 A   Q   P   Q   I
            1359          1368          1377          1386          1395          1404
CTG GCA GCC AGC TCT GCC TTT CCA CTG CCG GGA GTG CTG GGG GCC CAG CCT GGC
```

FIGURE 1D

```
      1413       1422       1431       1440       1449       1458
CCC CTG AAG AGA CAG CCA AGT GTC CAC ATA CTC CTC CCA GAG TGA GCT CTA 1467       1476       1485       1494       1503       1512
ACC AGG CTC ATT TGC TCT CTC CAC TAC TCA TCT CTG GAA TTA GCC GCT TAA ATA 1521       1530       1539       1548       1557       1566
CAG GTT TTT GTT GCT GAG ATG TGA GTG AAA CCA GCT AGT GTG TCA ACA GTG AAG 1575       1584       1593       1602       1611       1620
ACC TGG GGA CAG TTC TGC GTC TCA TTT CTG GAT TCC TAC CCC CTC TTC TAG TCT 1629       1638       1647       1656       1665       1674
TGC CCA AGT AGT CCT GCC AGG CAC ATG CCC CAT TTG GCA CAG GCC TGC ATT CTT 1683       1692       1701       1710       1719       1728
GTC GTG CCG TCC TGG GCC TCA GGC TGT CTG GGA GGG GAG ATG CTC ACA TTT GTA 1737       1746       1755       1764       1773       1782
CAG GCT ACA TAG ACT GGT GCA AGC AGT GCT GGA TTC CAG GAG TCT TGG CAT CTC 1791       1800       1809       1818       1827       1836
ATA GCT TGT CCC CGT GAG GAG TGA GCA GAG GGT CTG GGA TTT CTG CTT TCA GCA
```

FIGURE 1E

```
            1845      1854           1863      1872      1881      1890
AAA GCA GTC TGA CTC AGT GGG CAG AAT GGA GGG GCC CCT CTA GCC AGG CTC TTA 1899      1908           1917      1926      1935      1944
CGC CAT GGT TAT GAG CAG GTT GAT GAG GGT CCT TCG GCC AGC ACA ACC TTC CTC 1953      1962           1971      1980      1989      1998
CCT ACT CAC GGC ATG GAG TCT GAC TGC ATG GAA GTT CCA GAT CCT GAC AGA GAG 2007      2016           2025      2034      2043      2052
AAC TGG GAA GGA TCC AGG TTC GCT TCC GTT GGT AGT AGC TTG AGT CCC ATG CCT CCA 2061      2070           2079      2088      2097      2106
CCC TGC CAT CTG AGG AAG GGG TGA CAA GTG GTC AAG GAG CTG TGG CCA CAG ACT 2115      2124           2133      2142      2151      2160
TTT CCA GGG TGG TCC TTG GCA GGT GAG GTG CGT CTG TGC CAC CCT TGT CAG GAG 2169      2178           2187      2196      2205      2214
TCA TTG ACG ACG GGC CCC CCC TGG ACC CCC CGG GAC CTC AGA GTG GGG GCA GGC 2223      2232           2241      2250      2259      2268
AGA AGG GAG AAC CAG CTC AAG ACA TTT TGG AGG ATC TGG CCC TGG GGT TCT TCA
```

FIGURE 1F

```
              2277              2286              2295              2304              2313              2322
              GAG AAC ACC CTC TAG GGG CTT TGG GGA CAT GGC CTG TCC CCA CAT CCA GCA CTT
              2331              2340              2349              2358              2367              2376
              GCC TCC GCC ATG GTC ACT CGG CAG CCC TTT TCC CAG GAG AAG ACA CCT CTG GGA
              2385              2394              2403              2412              2421              2430
              GCC TGC TCA GTG CTT GTC CTG CCA TCC TGT GTC CTG GGA CTG AGG GTT ACT CCA
              2439              2448              2457              2466              2475              2484
              GTT GCT CTG TGT TGC ATA CTC TCC CCC GCA AGC CTG TGT ATG AAG AAT TGT CCC
              2493              2502              2511              2520              2529              2538
              CTG GCT TCC AGC AGG CCA TGG CTG GCT GTT TTG TGA CTG TTA CAT TGT GCA GGG
              2547              2556              2565              2574
              GTA ATT ATT AGC GTG GCT TTT ACA CTT AAA AAA AAA A 3'
```

FIGURE 1G

| | | | |
|---|---|---|---|
| 1 | MDVLSPLS-------------------------------- | | 638789 |
| 1 | AR------------VTVPEPGAAESRAPCGD-------SSGGCVRSAGASMDQSVAIQETL- | | g1399105 |
| 1 | VTVPEPGAAESRAPCGDSSGGCVRSAGASMDQSVAIQETL- | | g1019103 |
| 1 | MEPPLPVGAQPLA-----------------------------TVEGMEMKGPLREP- | | g1420920 |

| 9 | -------------------------------------- | | 638789 |
| 3 | -------------------------------------- | | g1399105 |
| 41 | AEGEYCVIAVQGVLCEGDSRQSRLLGLVRYRLEHGGQEHA | | g1019103 |
| 28 | ---CALT----------------------LAQRNGQYE | | g1420920 |

| 9 | -------------------------------------- | | 638789 |
| 3 | -------------------------------------- | | g1399105 |
| 81 | LFLYTHRRMAITGDDVSLDQIVPVSRDFTLEEVSPDGELY | | g1019103 |
| 41 | LIIQLHEK------EQHVQDIIPINSHFRCVQEAEETLLI | | g1420920 |

| 9 | -------------------------------------- | | 638789 |
| 3 | -------------------------------------- | | g1399105 |
| 121 | ILGSDVTVQLDTAELSLVFQLPFGSQTRMFLHEVARACPG | | g1019103 |
| 75 | DIASNSGCKIRVQGDWI--RERRFEIPDEEHCLK | | g1420920 |

| 9 | -------------------------------------- | | 638789 |
| 3 | -------------------------------------- | | g1399105 |
| 161 | FDSATRDPEFLWLSRYRCAELELEMPTPRGCNSALVTWPG | | g1019103 |
| 107 | FLSAVLAAQK---AQSQLLVPEQKDSSS---W-- | | g1420920 |

| 9 | -------------------------------------- | | 638789 |
| 3 | -------------------------------------- | | g1399105 |
| 201 | YATIGGGG--SNFDGL---RPNGKGVPMDQSSRGQDKPES | | g1019103 |
| 133 | YQKLDTKDKPSVFSGLLGFEDNFSSMNLDKKINSQNQPTG | | g1420920 |

| | | 638789 | g1399105 | g1019103 | g1420920 |

| Library | Lib Description | Abun | Pct Abun |
|---|---|---|---|
| PANCISM01 | pancreas, islet cells, NORM, WM | 2 | 0.1907 |
| SCORNON01 | spinal cord, 71 M, NORM | 1 | 0.1379 |
| BSTMNOT01 | brain stem, 72 M | 1 | 0.1214 |
| MUSCNOM01 | skeletal muscle, WM | 2 | 0.0861 |
| THP1NOT01 | THP-1 promonocyte cell line, untreated | 1 | 0.0571 |
| SYNORAT01 | synovium, elbow, rheumatoid, 51 F | 1 | 0.0478 |
| NERVMSM01 | multiple sclerosis, 46 M, NORM, WM | 2 | 0.0448 |
| BRSTNOT03 | breast, 54 F, match to BRSTTUT02 | 3 | 0.0441 |
| PENCNOT01 | penis, corpus cavernosum, 53 M | 1 | 0.0394 |
| COLNNOT09 | colon, 60 M, match to COLNTUT16 | 1 | 0.0390 |
| PROSNOT20 | prostate, 65 M, match to PROSTUT12 | 1 | 0.0336 |
| COLNNOT13 | colon, ascending, 28 M | 1 | 0.0311 |
| BRAITUT08 | brain tumor, astrocytoma, 47 M | 2 | 0.0293 |
| SCORNOT04 | spinal cord, 32 M | 1 | 0.0293 |
| LEUKNOT02 | white blood cells, 45 F | 1 | 0.0292 |
| COLNFET02 | colon, fetal F | 2 | 0.0286 |
| THYRTUT03 | thyroid tumor, benign, 17 M | 1 | 0.0276 |
| LNODNOT05 | lymph nodes, 14 F | 1 | 0.0271 |
| THP1AZS08 | THP-1 promonocyte cell line, treated AZ, SUB | 2 | 0.0269 |
| UTRSNOT08 | uterus, endometrium, 35 F | 1 | 0.0267 |
| HEAANOT01 | heart, coronary artery, 46 M | 1 | 0.0265 |
| HEAONOT03 | heart, aorta, 27 F | 1 | 0.0265 |
| BRAITUT13 | brain tumor, meningioma, 68 M | 1 | 0.0262 |
| COTRNOT01 | colon, transverse, Crohn's, 26 M | 1 | 0.0260 |

FIGURE 3A

| | | | |
|---|---|---|---|
| BONRFET01 | rib, fetal M | 1 | 0.0259 |
| SINTFET03 | small intestine, fetal F | 2 | 0.0259 |
| THYMNON04 | thymus, 3 M, NORM | 1 | 0.0257 |
| STOMFET01 | stomach, fetal F | 1 | 0.0255 |
| TLYMNOT02 | lymphocytes (non-adher PBMNC), M/F | 1 | 0.0254 |
| HEAONOT05 | heart, aorta, 17 F | 1 | 0.0252 |
| UTRSTUT04 | uterine tumor, leiomyoma, 34 F | 1 | 0.0250 |
| LUNGTUT13 | lung tumor, adenocarcinoma, 47 M | 1 | 0.0249 |
| PONSAZT01 | brain, pons, Alzheimer's, 74 M | 1 | 0.0249 |
| TMLR3DT02 | lymphocytes (non-adher PBMNC), M/F, 72-hr MLR | 1 | 0.0246 |
| PROSNOT15 | prostate, 66 M, match to PROSTUT10 | 1 | 0.0241 |
| SINJNOT02 | small intestine, jejunum, 8 F | 1 | 0.0241 |
| UCMCNOT02 | mononuclear cells | 1 | 0.0236 |
| LIVSFEM03 | liver/spleen, fetal M, NORM, WM | 1 | 0.0214 |
| BRSTNOM02 | breast, F, NORM, WM | 1 | 0.0206 |
| BRSTTUT03 | breast tumor, 58 F, match to BRSTNOT05 | 2 | 0.0197 |
| COLNTUT03 | colon tumor, 62 M, match to COLNNOT16 | 1 | 0.0196 |
| THYMNOT02 | thymus, 3 M | 1 | 0.0194 |
| HNT3AZT01 | hNT2 cell line, teratocarcinoma, treated AZ | 1 | 0.0191 |
| NEUTLPT01 | granulocytes, periph blood, M/F, treated LPS | 1 | 0.0173 |
| MUSCNOT07 | muscle, forearm, 38 F | 1 | 0.0154 |
| COLNNOT11 | colon, 60 M, match to COLNTUT16 | 1 | 0.0149 |
| NGANNOT01 | ganglioneuroma, 9 M | 2 | 0.0146 |
| PROSTUT05 | prostate tumor, 69 M, match to PROSNOT07 | 1 | 0.0145 |
| THYRNOT03 | thyroid tumor, adenoma, 28 F | 1 | 0.0138 |
| SPLNNOT04 | spleen, 2 M | 1 | 0.0128 |

FIGURE 3B

| | | |
|---|---|---|
| KIDNNOT05 | kidney, neonatal F | 1 | 0.0106 |
| EOSIHET02 | eosinophils, hypereosinophilia, 48 M | 1 | 0.0105 |
| OVARTUT01 | ovarian tumor, 43 F, match to OVARNOT03 | 1 | 0.0103 |
| UTRPNOM01 | uterus, F, NORM, WM | 1 | 0.0101 |
| MELANOM01 | melanocytes, M, NORM, WM | 1 | 0.0096 |
| BRSTTUT01 | breast tumor, 55 F, match to BRSTNOT02 | 1 | 0.0095 |
| BRAINOM01 | brain, infant F, NORM, WM | 2 | 0.0089 |
| CARDFEM01 | heart, fetal, NORM, WM | 1 | 0.0082 |
| UTRSNOT02 | uterus, 34 F | 1 | 0.0078 |
| LUNGFET03 | lung, fetal F | 1 | 0.0069 |
| PLACNOM02 | placenta, neonatal F, NORM, WM | 1 | 0.0056 |
| LIVSFEM02 | liver/spleen, fetal M, NORM, WM | 2 | 0.0053 |

FIGURE 3C

PHOSPHATIDYLINOSITOL 4,5-BISPHOSPHATE 5-PHOSPHATASE

This application is a divisional application of U.S. application Ser. No. 08/884,681, filed Jun. 27, 1997, now U.S. Pat. No. 5,955,338.

FIELD OF THE INVENTION

This invention relates to nucleic acid and amino acid sequences of a new phosphatidyl-inositol 4,5-bisphosphate 5-phosphatase and to the use of these sequences in the diagnosis, prevention, and treatment of disorders of cell proliferation and cell signaling.

BACKGROUND OF THE INVENTION

Protein phosphorylation is the ubiquitous strategy used to control the activities of eukaryotic cells. It is estimated that 10% of the proteins active in a typical mammalian cell are phosphorylated. The high energy phosphate which confers activation and is transferred from adenosine triphosphate molecules to a protein by protein kinases is subsequently removed from the protein by protein phosphatases. In this way, the phosphatases control most cellular signaling events that regulate cell growth and differentiation, cell-to-cell contacts, the cell cycle, and oncogenesis.

The inositol polyphosphate phosphatases include several monomer enzymes of different molecular weights (115–160 kD, 69–75 kD, and 32–43 kD) which hydrolyze inositol polyphosphates. Such phosphatases are known to remove the phosphate from the 3, 4, or 5 position of the inositol ring of several different substrates. For example, membrane-bound polyphosphoinositide phosphatase from rat brain utilizes phosphatidylinositol (4)phosphate, phosphatidylinositol (3)phosphate and phosphatidylinositol 4,5-bisphosphate (PIP2) as substrates. Phosphatidyl-inositol 4,5-bisphosphate 5 phosphatase preferentially removes the position 5 phosphate from PIP2, but its affinity for other positions or substrates is not fully known (Hope H. M. and L. J. Pike (1994) J. Biol. Chem. 269:23648–54; Jefferson and Majerus (1995; J. Biol. Chem. 270:9370–9377).

Hydrolysis of PIP2 produces diacylglycerol (DAG) and inositol triphosphate (IP3), both of which act as second messengers in the cell signaling pathways. DAG and IP3 release Ca2+ from intracellular stores (endoplasmic/sarcoplasmic reticulum) and promote Ca2+ influx from the extracellular fluid. The phosphatases that catalyze the removal of phosphate are positively and negatively regulated by the local concentration of various ions including $CA^-$, $Mg^-$, and $Li^-$.

Jefferson and Majerus (supra) expressed and studied a type II polyphosphate 5 phosphatase cloned from a human erythroleukemia cell cDNA library. Their protein was 942 amino acids in length; hydrolyzed inositol 1,4,5-triphosphate, inositol 1,4-bisphosphate, and PIP2; shared two potential binding/catalytic motifs (amino acids 472–483 and 545–570) with other phosphatases; and had a 3'CPNL motif that suggested isoprenylation and membrane association. They showed that antibodies raised against a recombinant 75 kD inositol (1,4,5) triphosphate 5 phosphatase also depleted phosphatidyl-inositol 4,5-bisphosphate 5 phosphatase activity from the cytosolic and membrane fractions of platelets; and they suggested that tissue specific expression and/or proteolytic processing of the larger phosphatases may be the source of the cytosolic phosphatases.

The discovery of a new human phosphatidylinositol 4,5-bisphosphate 5-phosphatase and the polynucleotides encoding it satisfies a need in the art by providing new compositions which are useful in the diagnosis, prevention, and treatment of disorders of cell proliferation and cell signaling.

SUMMARY OF THE INVENTION

The invention features a substantially purified polypeptide, phosphatidylinositol 4,5-bisphosphate 5-phosphatase (PBPP), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding PBPP under conditions suitable for the expression of the polypeptide; and b) recovering the polypeptide from the host cell culture.

The invention also provides a pharmaceutical composition comprising a substantially purified PBPP having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising at least a fragment of the amino acid sequence of SEQ ID NO:1.

Still further, the invention provides a purified agonist of the polypeptide of SEQ ID NO:1.

The invention also provides a method for treating or preventing an immune disorder comprising administering to a subject in need of such treatment an effective amount of an antagonist of PBPP.

The invention also provides a method for treating or preventing a cancer comprising administering to a subject in need of such treatment an effective amount of an antagonist of PBPP.

The invention also provides a method for treating or preventing a neuronal disorder comprising administering to a subject in need of such treatment an effective amount of an antagonist of PBPP.

The invention also provides a method for detecting a polynucleotide which encodes PBPP in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding PBPP in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F and 1G show the amino acid sequence (SEQ ID NO:1) and nucleic acid sequence (SEQ ID NO:2) of phosphatidylinositol 4,5-bisphosphate 5-phosphatase (PBPP). The alignment was produced using MACDNASIS PRO software (Hitachi Software Engineering Co. Ltd. San Bruno, Calif.).

FIGS. 2A, 2B, 2C, 2D, and 2E show the amino acid sequence alignments among PBPP (SEQ ID NO:1), a partial human phosphatidylinositol 4,5-bisphosphate 5-phosphatase (GI 1399105; SEQ ID NO:3), an inositol polyphosphate 5 phosphatase (GI 1019103; SEQ ID NO:4), and Lowe's oculocerebrorenal syndrome protein (GI 1420920; SEQ ID NO:5) produced using the multisequence alignment program of DNASTAR™ software (DNASTAR Inc, Madison Wis.).

FIGS. 3A, 3B, and 3C show the northern analysis for PBPP produced using the LIFESEQ™ database (Incyte Pharmaceuticals, Palo Alto Calif.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

PBPP, as used herein, refers to the amino acid sequences of substantially purified PBPP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to PBPP, increases or prolongs the duration of the effect of PBPP. Agonists may include proteins, nucleic acids, carbohydrates, or any other molecules which bind to and modulate the effect of PBPP.

An "allele" or "allelic sequence", as used herein, is an alternative form of the gene encoding PBPP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PBPP as used herein include those with deletions, insertions, or substitutions of different nucleotides resulting in a polynucleotide that encodes the same or a functionally equivalent PBPP. Included within this definition are polymorphisms which may or may not be readily detectable using a particular oligonucleotide probe of the polynucleotide encoding PBPP, and improper or unexpected hybridization to alleles, with a locus other than the normal chromosomal locus for the polynucleotide sequence encoding PBPP. The encoded protein may also be "altered" and contain deletions, insertions, or substitutions of amino acid residues which produce a silent change and result in a functionally equivalent PBPP. Deliberate amino acid substitutions may be made on the basis of similarity in polarity, charge, solubility, hydrophobicity, hydrophilicity, and/or the amphipathic nature of the residues as long as the biological or immunological activity of PBPP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of PBPP are preferably about 5 to about 15 amino acids in length and retain the biological activity or the immunological activity of PBPP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to PBPP, decreases the amount or the duration of the effect of the biological or immunological activity of PBPP. Antagonists may include proteins, nucleic acids, carbohydrates, antibodies or any other molecules which decrease the effect of PBPP.

As used herein, the term "antibody" refers to intact molecules as well as fragments thereof, such as Fab, F(ab')$_2$, and Fv, which are capable of binding the epitopic determinant. Antibodies that bind PBPP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic PBPP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding PBPP (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding PBPP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to PBPP or the encoded PBPP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear micro-chromosomes which may contain DNA sequences of 10K to 10M in size and contain all of the elements required for stable mitotic chromosome segregation and maintenance (Harrington, J. J. et al. (1997) Nat. Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of PBPP. For example, modulation may cause an increase or a decrease in protein activity, binding characteristics, or any other biological, functional or immunological properties of PBPP.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length PBPP and fragments thereof.

The term "sample", as used herein, is used in its broadest sense. A biological sample suspected of containing nucleic acid encoding PBPP, or fragments thereof, or PBPP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PBPP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human phosphatidylinositol 4,5-bisphosphate 5-phosphatase (hereinafter referred to as "PBPP"), the polynucleotides encoding PBPP, and the use of these compositions for the diagnosis, prevention, or treatment of disorders of cell proliferation and cell signaling.

Nucleic acids encoding the PBPP of the present invention were first identified in Incyte Clone 638789 from the breast cDNA library (BRSTNOT03) using a computer search for amino acid sequence alignments. A consensus sequence, SEQ ID NO:2, was derived from the following overlapping and/or extended nucleic acid sequences: Incyte Clones 344258 (THYMNOT02), 638789 and 1004117 (BRSTNOT03), 1440246 (THYRNOT03), and 1684709 (PROSNOT15).

Figure 2B:
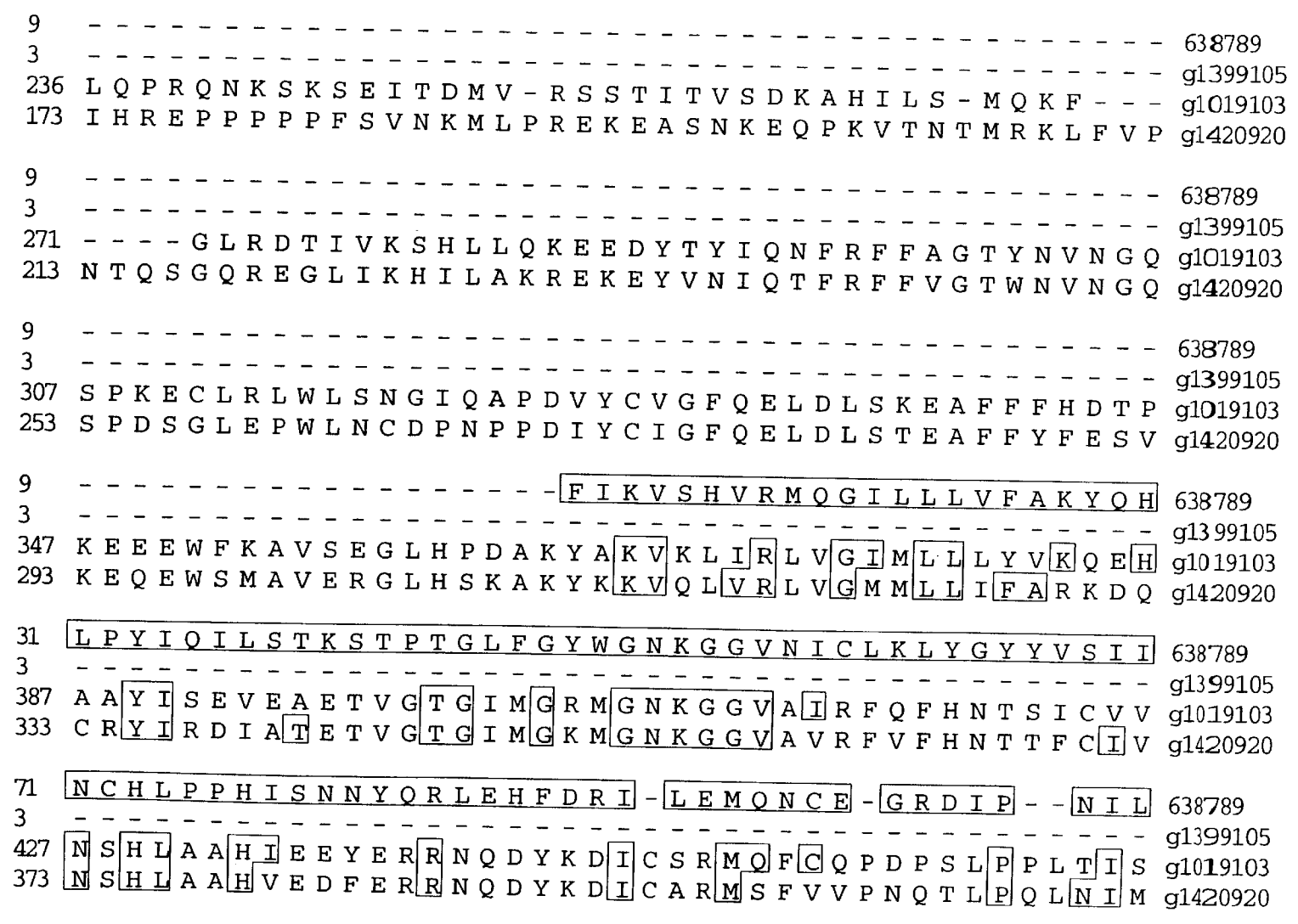
Figure 2C:
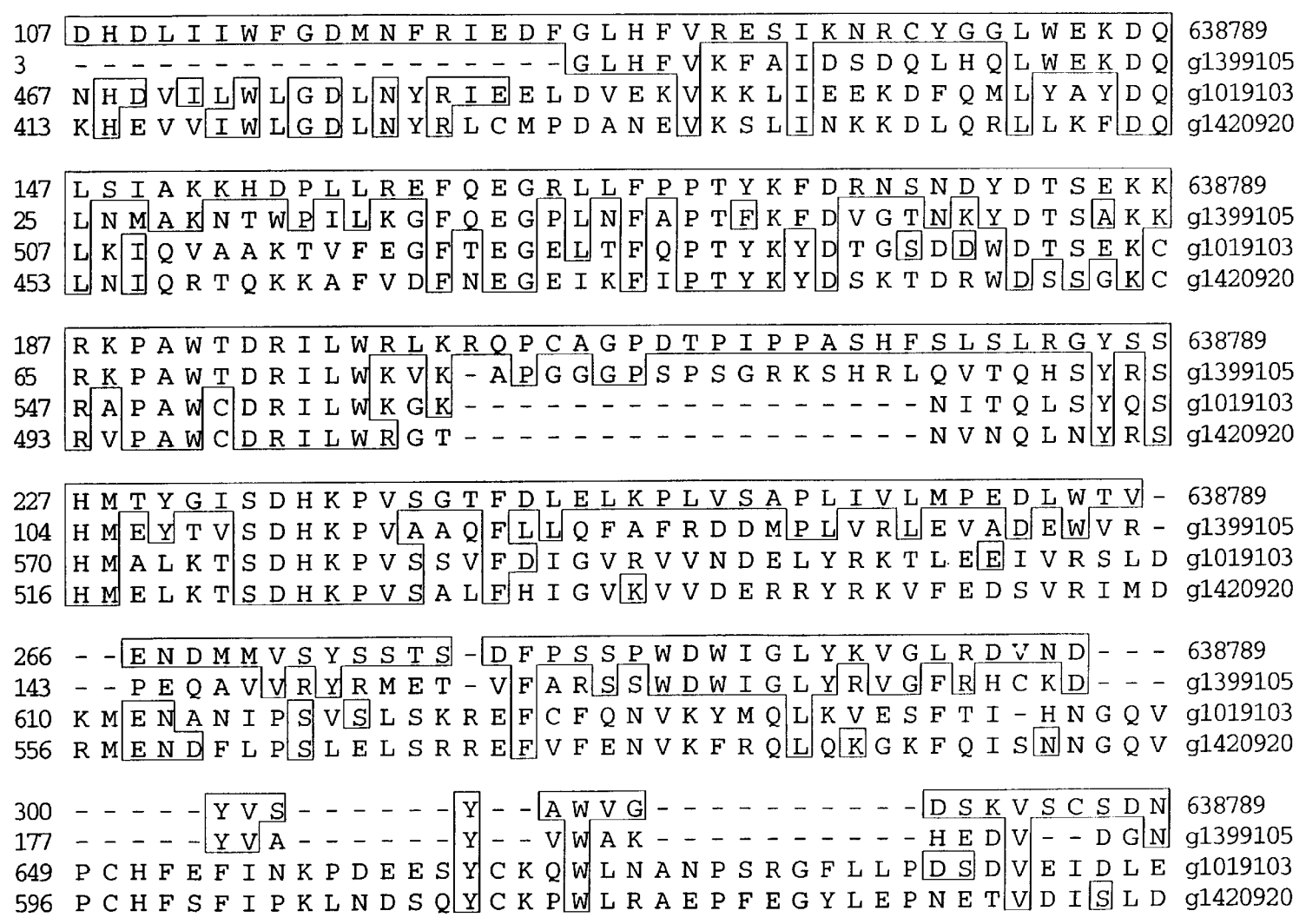
Figure 2D:
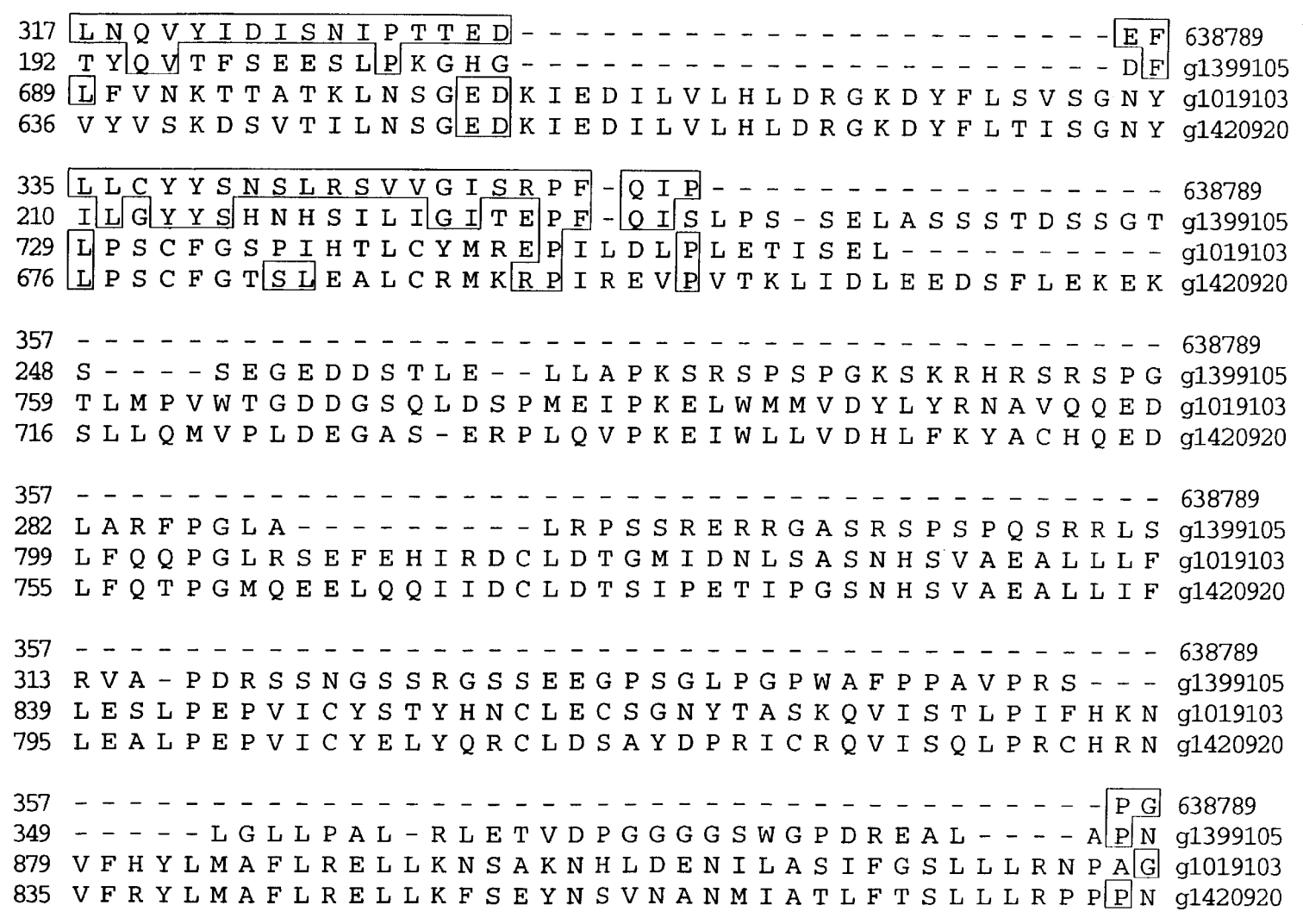
Figure 2E:
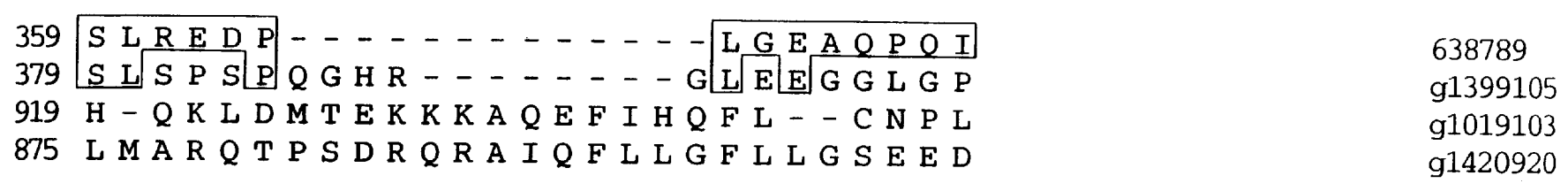

In one embodiment, the invention encompasses a polypeptide comprising the amino acid sequence of SEQ ID NO:1, as shown in FIGS. 1A–G. PBPP is 372 amino acids in length and has potential phosphorylation sites at S38, S132, T170, S183, T192, S275, S282, R295, S312, T329, T330, and S359. As shown in FIGS. 2A–E, PBPP has chemical and structural homology with a partial human phosphatidylinositol 4,5-bisphosphate 5-phosphatase (GI 1399105; SEQ ID NO:3), an inositol polyphosphate 5 phosphatase (GI 1019103; SEQ ID NO:4), and Lowe's oculocerebrorenal syndrome protein (GI 1420920; SEQ ID NO:5). Two potential catalysis or binding sites conserved among these related molecules are N104-D123 and D181-K200. PBPP has 124 unique residues 5' of the published sequence for the partial human phosphatidylinositol 4,5-bisphosphate 5-phosphatase; beyond residue F124, they share 64% identity. The lack of an isoprenylation motif suggests that PBPP is a cytosolic enzyme. Northern analysis shows the expression of this sequence in various libraries, at least 31% of which are associated with inflammation or immune disorders, at least 26% are from immortalized or cancerous cells or tissues at least 11% of are from fetal or infant tissues and at least 11% of which involve tissues of the neuronal tissues (FIGS. 3A–C) Of particular note is the association of PBPP with libraries undergoing or associated with cell proliferation.

The invention also encompasses PBPP variants. A preferred PBPP variant is one having at least 80%, and more preferably at least 90%, amino acid sequence identity to the PBPP amino acid sequence (SEQ ID NO:1) and which retains at least one biological, immunological, or other functional characteristic or activity of PBPP. A most preferred PBPP variant is one having at least 95% amino acid sequence identity to SEQ ID NO:1.

The invention also encompasses polynucleotides which encode PBPP. Accordingly, any nucleic acid sequence which encodes the amino acid sequence of PBPP can be used to produce recombinant molecules which express PBPP. In a particular embodiment, the invention encompasses the polynucleotide comprising the nucleic acid sequence of SEQ ID NO:2 as shown in FIGS. 1A–G.

It will be appreciated by those skilled in the art that as a result of the degeneracy of the genetic code, a multitude of nucleotide sequences encoding PBPP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PBPP, and all such variations are to be considered as being specifically disclosed.

Although nucleotide sequences which encode PBPP and its variants are preferably capable of hybridizing to the nucleotide sequence of the naturally occurring PBPP under appropriately selected conditions of stringency, it may be advantageous to produce nucleotide sequences encoding PBPP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PBPP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PBPP and its derivatives, entirely by synthetic chemistry. After production. the synthetic sequence may be inserted into any of the many available expression vectors and cell systems using reagents that are well known in the art. Moreover, synthetic chemistry may be used to introduce mutations into a sequence encoding PBPP or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by Gibco/BRL (Gaithersburg, Md.). Preferably, the process is automated with machines such as the MICROLAB 2200 (Hamilton, Reno, Nev., Peltier thermal cycler (PTC200; MJ Research, Watertown, Mass.), and the ABI CATALYST and 373 and 377 DNA sequencers (Perkin Elmer).

The nucleic acid sequences encoding PBPP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplifly or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTORFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PBPP may be used in recombinant DNA molecules to direct expression of PBPP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PBPP.

As will be understood by those of skill in the art, it may be advantageous to produce PBPP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PBPP encoding sequences for a variety of reasons, including but not limited to, alterations which modify the cloning, processing, and/or expression of the gene product. DNA shuffling by random fragmentation and PCR reassembly of gene fragments and synthetic oligo- nucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PBPP may be ligated to a heterologous sequence to encode a fusion protein. For example, to screen peptide libraries for inhibitors of PBPP activity, it may be useful to encode a chimeric PBPP protein that can be recognized by a commercially available antibody. A fusion protein may also be engineered to contain a cleavage site located between the PBPP encoding sequence and the heterologous protein sequence, so that PBPP may be cleaved and purified away from the heterologous moiety.

In another embodiment, sequences encoding PBPP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of PBPP, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* W H Freeman and Co., New York, N.Y.). The composition of the synthetic peptides may be confirmed by amino acid analysis or sequencing (e.g., the Edman degradation procedure; Creighton, supra). Additionally, the amino acid sequence of PBPP, or any part thereof, may be altered during direct synthesis and/or combined using chemical methods with sequences from other proteins, or any part thereof, to produce a variant polypeptide.

In order to express a biologically active PBPP, the nucleotide sequences encoding PBPP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PBPP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding PBPP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PBPP, vectors based on SV40 or EBV may be used with an appropriate selectable marker.

In bacterial systems, a number of expression vectors may be selected depending upon the use intended for PBPP. For example, when large quantities of PBPP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding PBPP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PBPP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express PBPP. For example, in one such system, *Autographa californica* nuclear polyhedrosis virus (AcNPV) is used as a vector to express foreign genes in *Spodoptera frugiperda* cells or in Trichoplusia larvae. The sequences encoding PBPP may be cloned into a non-essential region of the virus, such as the polyhedrin gene, and placed under control of the polyhedrin promoter. Successful insertion of PBPP will render the polyhedrin gene inactive and produce recombinant virus lacking coat protein. The recombinant viruses may then be used to infect, for example, *S. frugiperda* cells or Trichoplusia larvae in which PBPP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding PBPP may be ligated into an adenovirus transcription/translation complex consisting of the late promoter and tripartite leader sequence. Insertion in a non-essential E1 or E3 region of the viral genome may be used to obtain a viable virus which is capable of expressing PBPP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PBPP. Such signals include the ATG initiation codon and adjacent sequences. In cases where sequences encoding PBPP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g. CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express PBPP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PBPP is inserted within a marker gene sequence, transformed cells containing sequences encoding PBPP can be identified by the absence of marker gene function. Alternatively, a marker gene can be placed in tandem with a sequence encoding PBPP under the control of a single promoter. Expression of the marker gene in response to induction or selection usually indicates expression of the tandem gene as well.

Alternatively, host cells which contain the nucleic acid sequence encoding PBPP and express PBPP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding PBPP can be detected by DNA-DNA or DNA-RNA hybridization or amplification using probes or fragments or fragments of polynucleotides encoding PBPP. Nucleic acid amplification based assays involve the use of oligonucleotides or oligomers based on the sequences encoding PBPP to detect transformants containing DNA or RNA encoding PBPP.

A variety of protocols for detecting and measuring the expression of PBPP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PBPP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PBPP include oligolabeling, nick translation, end-labeling or PCR amplification using a labeled nucleotide. Alternatively, the sequences encoding PBPP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp. (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PBPP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PBPP may be designed to contain signal sequences which direct secretion of PBPP through a prokaryotic or eukaryotic cell membrane. Other constructions may be used to join sequences encoding PBPP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PBPP may be used to facilitate purification. One such expression vector provides for expression of a fusion protein containing PBPP and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying PBPP from the fusion protein. A discussion of vectors which contain fusion proteins is provided in Kroll, D. J. et al. (1993; DNA Cell Biol. 12:441–453).

In addition to recombinant production, fragments of PBPP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of PBPP may be chemically synthesized separately and combined using chemical methods to produce the full length molecule.

Therapeutics

Chemical and structural homology exists among PBPP, a partial human phosphatidylinositol 4,5-bisphosphate 5-phosphatase (GI 1399105; SEQ ID NO:3), an inositol polyphosphate 5 phosphatase (GI 1019103; SEQ ID NO:4), and Lowe's oculocerebrorenal syndrome protein (GI 1420920; SEQ ID NO:5). In addition, PBPP is expressed in many cancerous and fetal/infant cell and tissues; therefore, PBPP appears to play a role in cell proliferation or cell signaling.

In one embodiment, an antagonist of PBPP may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds PBPP may be used directly as an antagonist or indirectly as a targeting or delivery mechanism for bringing a pharmaceutical agent to cells or tissue which express PBPP.

In another embodiment, a vector expressing the complement of the polynucleotide encoding PBPP may be administered to a subject to treat or prevent an immune disorder including, but not limited to, those described above.

In one embodiment, an antagonist of PBPP may be administered to a subject to prevent or treat a cancer. Such cancers may include, but are not limited to, adenocarcinoma, leukemia, lymphoma, melanoma, myeloma, sarcoma, and teratocarcinoma; and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PBPP may be used directly as an antagonist or indirectly as a targeting or delivery mechanism for bringing a pharmaceutical agent to cells or tissue which express PBPP.

In another embodiment, a vector expressing the complement of the polynucleotide encoding PBPP may be administered to a subject to treat or prevent a cancer including, but not limited to, those described above.

In one embodiment, an antagonist of PBPP may be administered to a subject to prevent or treat a neuronal disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. In one aspect, an antibody which specifically bind PBPP may be used directly as an antagonist or indirectly as a targeting or delivery mechanism for bringing a pharmaceutical agent to cells or tissue which express PBPP.

In another embodiment, a vector expressing the complement of the polynucleotide encoding PBPP may be administered to a subject to treat or prevent a neuronal disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PBPP may be produced using methods which are generally known in the art. In particular, purified PBPP may be used to produce antibodies or to screen libraries of pharmaceutical agents to identify those which specifically bind PBPP.

Antibodies to PBPP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PBPP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium paryum* are especially preferable.

It is preferred that the oligopeptides, peptides, or fragments used to induce antibodies to PBPP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PBPP amino acids may be fused with those of another protein such as keyhole limpet hemocyanin and antibody produced against the chimeric molecule.

Monoclonal antibodies to PBPP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497: Kozbor, D. et al. (1985) J. Immunol. Methods 81:31–42; Cote, R. J. et al. (1983) Proc. Natl. Acad. Sci. 80:2026–2030; Cole, S.P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M.S. et al. (1984) Nature 312:604–608; Takeda, S. et al. (1985) Nature 314:452–454). Alternatively, techniques described for the production of single chain antibodies may be adapted, using methods known in the art, to produce PBPP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for PBPP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PBPP and its specific antibody. A two-site, monoclonal-based immunoassay utilizing monoclonal antibodies reactive to two non-interfering PBPP epitopes is preferred, but a competitive binding assay may also be employed (Maddox, supra).

In another embodiment of the invention, the polynucleotides encoding PBPP, or any fragment or complement thereof, may be used for therapeutic purposes. In one aspect, the complement of the polynucleotide encoding PBPP may be used in situations in which it would be desirable to block the transcription of the mRNA. In particular, cells may be transformed with sequences complementary to polynucleotides encoding PBPP. Thus, complementary molecules or fragments may be used to modulate PBPP activity, or to achieve regulation of gene function. Such technology is now well known in the art, and sense or antisense oligonucleotides or larger fragments, can be designed from various locations along the coding or control regions of sequences encoding PBPP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PBPP. These techniques are described both in Sambrook et al. (supra) and in Ausubel et al. (supra).

Genes encoding PBPP can be turned off by transforming a cell or tissue with expression vectors which express high levels of a polynucleotide or fragment thereof which encodes PBPP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PBPP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ibosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PBPP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PBPP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PBPP, antibodies to PBPP, mimetics, agonists, antagonists, or inhibitors of PBPP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PBPP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PBPP or fragments thereof, antibodies of PBPP, agonists, antagonists or inhibitors of PBPP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PBPP may be used for the diagnosis of conditions or diseases characterized by expression of PBPP, or in assays to monitor patients being treated with PBPP, agonists, antagonists or inhibitors. The antibodies useful for diagnostic purposes may be prepared in the same manner as those described above for therapeutics. Diagnostic assays for PBPP include methods which utilize the antibody and a label to detect PBPP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PBPP are known in the art and provide a basis for diagnosing altered or abnormal levels of PBPP expression. Normal or standard values for PBPP expression are established by combining body fluids or cell extracts taken from normal mammalian subjects, preferably human, with antibody to PBPP under conditions suitable for complex formation. The amount of standard complex formation may be quantified by various methods, but preferably by photometric, means. Quantities of PBPP expressed in subject, control and disease, samples from biopsied tissues are compared with the standard values. Deviation between standard and subject values establishes the parameters for diagnosing disease.

In another embodiment of the invention, the polynucleotides encoding PBPP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PBPP may be correlated with disease. The diagnostic assay may be used to distinguish between absence, presence, and excess expression of PBPP, and to monitor regulation of PBPP levels during therapeutic intervention.

In one aspect, hybridization with PCR probes which are capable of detecting polynucleotide sequences, including genomic sequences. encoding PBPP or closely related molecules, may be used to identify nucleic acid sequences which encode PBPP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PBPP, alleles, or related sequences.

Probes may also be used for the detection of related sequences, and should preferably contain at least 50% of the nucleotides from any of the PBPP encoding sequences. The hybridization probes of the subject invention may be DNA or RNA and derived from the nucleotide sequence of SEQ ID NO:2 or from genomic sequence including promoter, enhancer elements, and introns of the naturally occurring PBPP.

Means for producing specific hybridization probes for DNAs encoding PBPP include the cloning of nucleic acid sequences encoding PBPP or PBPP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PBPP may be used for the diagnosis of conditions or diseases which are associated with expression of PBPP. Examples of such conditions or disorders include immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma; cancers such as adenocarcinoma, leukemia, lymphoma, melanoma, myeloma, sarcoma, and teratocarcinoma; and particularly cancers of the adrenal gland, bladder, bone. bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and neuronal disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. The polynucleotide sequences encoding PBPP may be used in Southern or northern analysis, dot blot, or other membrane-based technologies; in PCR technologies; or in dipstick, pin, ELISA assays or microarrays utilizing fluids or tissues from patient biopsies to detect altered PBPP expression. Such qualitative or quantitative methods are well known in the art.

In a particular aspect, the nucleotide sequences encoding PBPP may be useful in assays that detect activation or induction of various cancers, particularly those mentioned above. The nucleotide sequences encoding PBPP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PBPP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PBPP, a normal or standard profile for expression is established. This may be accomplished by combining body fluids or cell extracts taken from normal subjects, either animal or human, with a sequence, or a fragment thereof, which encodes PBPP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PBPP may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PBPP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Nati. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state. In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence.

The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations. variants or polymorphisms among samples.

In another embodiment of the invention, the nucleic acid sequences which encode PBPP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) Human Chromosomes: *A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PBPP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PBPP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PBPP and the agent being tested, may be measured.

Another technique for drug screening which may be used provides for high throughput screening of compounds having suitable binding affinity to the protein of interest as described in published PCT application WO84/03564. In this method, as applied to PBPP large numbers of different small test compounds are synthesized on a solid substrate, such as plastic pins or some other surface. The test compounds are reacted with PBPP, or fragments thereof, and washed. Bound PBPP is then detected by methods well known in the art. Purified PBPP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PBPP specifically compete with a test compound for binding PBPP. In this manner, the antibodies can be used to detect the presence of any peptide which shares one or more antigenic determinants with PBPP.

In additional embodiments, the nucleotide sequences which encode PBPP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRSTNOT03 cDNA Library Construction

The BRSTNOT03 cDNA library was constructed from tissue removed from the normal breast of a 54 year old female (lot #0025B; Mayo Clinic, Rochester Minn.). The frozen tissue was immediately homogenized and lysed using a Brinkmann Homogenizer Polytron PT-3000 (Brinkmann Instruments Inc, Westbury N.Y.) in guanidinium isothiocyanate solution.

The BRSTTUT02 cDNA library was constructed from breast tumor removed from a 54 year old female (lot #0025A; Mayo Clinic, Rochester Minn.). The frozen tissue was immediately homogenized and lysed using a Brinkmann Homogenizer Polytron-PT 3000 in guanidinium isothiocyanate solution. Lysates were then loaded on a 5.7 M CsCI cushion and ultracentrifuged in a SW28 swinging bucket rotor for 18 hours at 25,000 rpm at ambient temperature. The RNA was extracted once with acid phenol at pH 4.0, once with phenol chloroform at pH 8.0, precipitated using 0.3 M sodium acetate and 2.5 volumes of ethanol, resuspended in DEPC-treated water, and treated with DNase for 25 min at 37° C. The reaction was stopped with an equal volume of acid phenol, and the RNA was isolated with the Qiagen Oligotex kit (QIAGEN Inc, Chatsworth Calif.) and used to construct the cDNA library.

The RNA was handled according to the recommended protocols in the SuperScript Plasmid System for cDNA synthesis and plasmid cloning (Cat. #18248-013; Gibco/BRL). cDNAs were fractionated on a Sepharose CL4B column (Cat. #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of cDNA Clones

Plasmid DNA was released from the cells and purified using the Miniprep Kit (Cat. # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. # 22711, Gibco/BRL) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @ 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J. Mol. Biol. 94:441f), using a Hamilton Micro Lab 2200 (Hamilton, Reno Nev.) in combination with four Peltier Thermal Cyclers (PTC200; M J Research, Watertown Mass.) and Applied Biosystems 377 or 373 DNA Sequencing Systems (Perkin Elmer), and reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S F (1993) J. Mol. Evol. 36:290–300; Altschul, S F et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc. Nat. Acad. Sci. 90:5873–7) and incorporated herein by reference, searches matches between a query sequence and a database sequence, to evaluate the statistical significance of any matches found, and to report only those matches which satisfy the user-selected threshold of significance. In this application threshold was set at 10–25 for nucleotides and 10–14 for peptides.

Incyte nucleotide sequence were searched against the GenBank databases for pri=primate rod=rodent, and mam=mammalian sequences, and deduced amino acid sequences from the same clones are searched against GenBank functional protein databases, mamp=mammalian, vrtp=vertebrate and eukp=eukaryote, for homology. The relevant database for a particular match were reported as a Glxxx+p (where xxx is for pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PBPP occurs. Abundance and percent abundance are also reported. Abundance directly reflects the number of times a particular transcript is represented in a cDNA library, and percent abundance is abundance divided by the total number of sequences examined in the cDNA library.

V Extension of PBPP Encoding Polynucleotides

The nucleic acid sequence of the Incyte Clone 368789 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2×Carb. The following day, several colonies were randomly picked from each plate and cultured in 150 μl of liquid LB/2×Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension. and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μl Ci of [$\gamma$-$^{32}$P] adenosine triphosphate (Amersharn) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the PBPP-encoding sequence, or any part thereof, is used to decrease or inhibit expression of naturally occurring PBPP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of PBPP, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PBPP-encoding transcript.

IX Expression of PBPP

Expression of PBPP is accomplished by subcloning the cDNAs into appropriate vectors and transforming the vectors into host cells. In this case, the cloning vector is also used to express PBPP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of PBPP into the bacterial growth media which can be used directly in the following assay for activity.

X Demonstration of PBPP Activity

An room temperature assay for 5-phosphatase activity using tritiated phosphatidylinositol 4,5-bisphosphate is described in Matzaris et al. (1994; J. Biol. Chem 269:3397–3402). In vitro, the presence of Mg+ and dithiothreitol may enhance hydrolysis.

XI Production of PBPP Specific Antibodies

PBPP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic. blocking with 1% BSA. reacting with rabbit antisera, washing, and reacting with radio iodinated. goat anti-rabbit IgG.

XII Purification of Naturally Occurring PBPP Using Specific Antibodies

Naturally occurring or recombinant PBPP is substantially purified by immunoaffinity chromatography using antibodies specific for PBPP. An immunoaffinity column is constructed by covalently coupling PBPP antibody to an activated chromatographic resin, such as CNBr-activated Sepharose (Pharmacia & Upjohn). After the coupling, the resin is blocked and washed according to the manufacturer's instructions.

Media containing PBPP is passed over the immunoaffinity column, and the column is washed under conditions that allow the preferential absorbance of PBPP (e.g., high ionic strength buffers in the presence of detergent). The column is eluted under conditions that disrupt antibody/PBPP binding (eg, a buffer of pH 2–3 or a high concentration of a chaotrope, such as urea or thiocyanate ion), and PBPP is collected.

XIII Identification of Molecules Which Interact with PBPP

PBPP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled PBPP, washed and any wells with labeled PBPP complex are assayed. Data obtained using different concentrations of PBPP are used to calculate values for the number, affinity, and association of PBPP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified polypeptide comprising an amino acid sequence selected from the group consisting of
   a) an amino acid sequence of SEQ ID NO:1, and
   b) an amino acid sequence having at least 90% sequence identity to the sequence of SEQ ID NO:1, and having phosphatidylinositol 4,5-bisphosphate 5-phosphatase activity.

2. A polypeptide of claim 1 having at least 90% amino acid identity to SEQ ID NO:1 and having phosphatidylinositol 4,5-bisphosphate 5-phosphatase activity.

3. A composition comprising a substantially purified polypeptide of claim 1 having phosphatidylinositol 4,5-bisphosphate 5-phosphatase activity in conjunction with a suitable pharmaceutical carrier.

4. A polypeptide of claim 1, having the amino acid sequence of SEQ ID NO:1.

5. A composition comprising a polypeptide of claim 4 having phosphatidylinositol 4,5-bisphosphate 5-phosphatase activity in conjunction with a suitable pharmaceutical carrier.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 372 amino acids
      (B) TYPE: amino acid
      (C) STRANDEDNESS: single
      (D) TOPOLOGY: linear (vii) IMMEDIATE SOURCE:
      (A) LIBRARY: BRSTNOT03
      (B) CLONE: 638789

(xi) SEQUENCE DESCRIPTION: SEQ ID NO:1:

```
Met Asp Val Leu Ser Pro Leu Ser Phe Ile Lys Val Ser His Val Arg
 1               5                  10                  15

Met Gln Gly Ile Leu Leu Leu Val Phe Ala Lys Tyr Gln His Leu Pro
             20                  25                  30

Tyr Ile Gln Ile Leu Ser Thr Lys Ser Thr Pro Thr Gly Leu Phe Gly
         35                  40                  45

Tyr Trp Gly Asn Lys Gly Gly Val Asn Ile Cys Leu Lys Leu Tyr Gly
 50                  55                  60

Tyr Tyr Val Ser Ile Ile Asn Cys His Leu Pro Pro His Ile Ser Asn
65                   70                  75                  80

Asn Tyr Gln Arg Leu Glu His Phe Asp Arg Ile Leu Glu Met Gln Asn
                 85                  90                  95

Cys Glu Gly Arg Asp Ile Pro Asn Ile Leu Asp His Asp Leu Ile Ile
             100                 105                 110

Trp Phe Gly Asp Met Asn Phe Arg Ile Glu Asp Phe Gly Leu His Phe
         115                 120                 125

Val Arg Glu Ser Ile Lys Asn Arg Cys Tyr Gly Gly Leu Trp Glu Lys
130                 135                 140

Asp Gln Leu Ser Ile Ala Lys Lys His Asp Pro Leu Leu Arg Glu Phe
145                 150                 155                 160

Gln Glu Gly Arg Leu Leu Phe Pro Pro Thr Tyr Lys Phe Asp Arg Asn
                165                 170                 175

Ser Asn Asp Tyr Asp Thr Ser Glu Lys Lys Arg Lys Pro Ala Trp Thr
            180                 185                 190

Asp Arg Ile Leu Trp Arg Leu Lys Arg Gln Pro Cys Ala Gly Pro Asp
        195                 200                 205

Thr Pro Ile Pro Pro Ala Ser His Phe Ser Leu Ser Leu Arg Gly Tyr
210                 215                 220

Ser Ser His Met Thr Tyr Gly Ile Ser Asp His Lys Pro Val Ser Gly
225                 230                 235                 240

Thr Phe Asp Leu Glu Leu Lys Pro Leu Val Ser Ala Pro Leu Ile Val
                245                 250                 255

Leu Met Pro Glu Asp Leu Trp Thr Val Glu Asn Asp Met Met Val Ser
            260                 265                 270

Tyr Ser Ser Thr Ser Asp Phe Pro Ser Ser Pro Trp Asp Trp Ile Gly
        275                 280                 285

Leu Tyr Lys Val Gly Leu Arg Asp Val Asn Asp Tyr Val Ser Tyr Ala
290                 295                 300
```

```
Trp Val Gly Asp Ser Lys Val Ser Cys Ser Asp Asn Leu Asn Gln Val
305                 310                 315                 320

Tyr Ile Asp Ile Ser Asn Ile Pro Thr Thr Glu Asp Glu Phe Leu Leu
                325                 330                 335

Cys Tyr Tyr Ser Asn Ser Leu Arg Ser Val Val Gly Ile Ser Arg Pro
                340                 345                 350

Phe Gln Ile Pro Pro Gly Ser Leu Arg Glu Asp Pro Leu Gly Glu Ala
            355                 360                 365

Gln Pro Gln Ile
        370

(2) INFORMATION FOR SEQ ID NO:2:

(i) SEQUENCE CHARACTERISTICS:
        (A) LENGTH: 2573 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT03
        (B) CLONE: 638789

(xi) SEQUENCE DESCRIPTION: SEQ ID NO:2:
```

| | | | | | |
|---|---|---|---|---|---|
| GAAGGCTCAG | CATACACGTC | GTGACTTGGA | ACGTGGCTTC | GGCAGCGCCC | CTCGAGCTCT | 60 |
| CAGTGACCTG | CTTCAGCTGA | CAACCGGAA | CCTCAATCTT | GACATATATG | TTATTGGTTT | 120 |
| GCAGGAATTG | AACTCTGGGA | TCATAAGCCT | CCTTTCCGAT | GCTGCCTTTA | ATGACTCGTG | 180 |
| GAGCAGTTTC | CTCATGGATG | TGCTTTCCCC | TCTGAGCTTC | ATCAAGGTCT | CCCATGTCCG | 240 |
| TATGCAGGGG | ATCCTCTTAC | TGGTCTTTGC | CAAGTATCAG | CATTTGCCCT | ATATCCAGAT | 300 |
| TCTGTCTACT | AAATCCACCC | CCACTGGCCT | GTTTGGGTAC | TGGGGGAACA | AAGGTGGAGT | 360 |
| CAACATCTGC | CTGAAGCTTT | ATGGCTACTA | TGTCAGCATC | ATCAACTGCC | ACCTGCCTCC | 420 |
| CCACATTTCC | AACAATTACC | AGCGGCTGGA | GCACTTTGAC | CGGATCCTGG | AGATGCAGAA | 480 |
| TTGTGAGGGG | CGAGACATCC | CAAACATCCT | GGACCACGAC | CTCATTATCT | GGTTTGGAGA | 540 |
| CATGAACTTT | CGGATCGAGG | ACTTTGGGTT | GCACTTTGTT | CGGGAATCCA | TTAAAAATCG | 600 |
| GTGCTACGGT | GGCCTGTGGG | AGAAGGACCA | GCTCAGCATT | GCCAAGAAAC | ATGACCCGCT | 660 |
| GCTCCGGGAG | TTCCAGGAGG | CCGCCTACT | CTTCCCGCCC | ACCTACAAGT | TGATAGGAA | 720 |
| CTCCAACGAC | TATGACACCA | GTGAGAAAAA | ACGCAAGCCT | GCATGGACCG | ATCGCATCCT | 780 |
| GTGGAGGCTG | AAGCGGCAGC | CCTGTGCTGG | CCCCGACACT | CCCATACCGC | CGGCGTCACA | 840 |
| CTTCTCCTTG | TCTCTGAGGG | GCTACAGCAG | CCACATGACG | TACGGCATCA | GCGACCACAA | 900 |
| GCCTGTCTCC | GGCACGTTCG | ACTTGGAGCT | GAAGCCATTG | GTGTCTGCTC | CGCTGATCGT | 960 |
| CCTGATGCCC | GAGGACCTGT | GGACCGTGGA | AAATGCATG | ATGGTCAGCT | ACTCTTCAAC | 1020 |
| CTCGGACTTC | CCCAGCAGCC | CGTGGGACTG | GATTGGACTG | TACAAGGTGG | GGCTGCGGGA | 1080 |
| CGTTAATGAC | TACGTGTCCT | ATGCCTGGGT | CGGGGACAGC | AAGGTCTCCT | GCAGCGACAA | 1140 |
| CCTGAACCAG | GTTTACATCG | ACATCAGCAA | TATCCCTACC | ACTGAAGATG | AGTTTCTCCT | 1200 |
| CTGTTACTAC | AGCAACAGTC | TGCGTTCTGT | GGTGGGGATA | AGCAGACCCT | TCCAGATCCC | 1260 |
| GCCTGGCTCC | TTGAGGGAGG | ACCCACTGGG | TGAAGCACAG | CCACAGATCT | GAGCCAGGAT | 1320 |
| GGGAGTGAAT | CCCAGGCGGA | GGCCAGAGCT | GGCAGCCAGC | TCTGCCTTTC | CACTGCCGGG | 1380 |
| AGTGCTGGGG | GCCCAGCCTG | GCCCCCTGAA | GAGACAGCCA | AGTGTCGTCC | ACATACTCCT | 1440 |
| CCCAGAGTGA | GCTCTAACCA | GGCTCATTTG | CTCTCTCCAC | TACTCATCTC | TGGAATTAGC | 1500 |

-continued

```
CGCTTAAATA CAGGTTTTTG TTGCTGAGAT GTGAGTGAAA CCAGCTAGTG TGTCAACAGT   1560

GAAGACCTGG GGACAGTTCT GCGTCTCATT TCTGGATTCC TACCCCCTCT TCTAGTCTTG   1620

CCCAAGTAGT CCTGCCAGGC ACATGCCCCA TTTGGCACAG GCCTGCATTC TTGTCGTGCC   1680

GTCCTGGGCC TCAGGCTGTC TGGGAGGGGA GATGCTCACA TTTGTACAGG CTACATAGAC   1740

TGGTGCAAGC AGTGCTGGAT TCCAGGAGTC TTGGCATCTC ATAGCTTGTC CCCGTGAGGA   1800

GTGAGCAGAG GGTCTGGGAT TTCTGCTTTC AGCAAAAGCA GTCTGACTCA GTGGGCAGAA   1860

TGGAGGGGCC CCTCTAGCCA GGCTCTTACG CCATGGTTAT GAGCAGGTTG ATGAGGGTCC   1920

TTCGGCCAGC ACAACCTTCC TCCCTACTCA CGGCATGGAG TCTGACTGCA TGGAAGTTCC   1980

AGATCCTGAC AGAGAGAACT GGGAAGGATC CAGGTTCGCT TCCGTTGGTA GCTTGAGTCC   2040

CATGCCTCCA CCCTGCCATC TGAGGAAGGG GTGACAAGTG GTCAAGGAGC TGTGGCCACA   2100

GACTTTTCCA GGGTGGTCCT TGGCAGGTGA GGTGCGTCTG TGCCACCCTT GTCAGGAGTC   2160

ATTGACGACG GGCCCCCCCT GGACCCCCCG GGACCTCAGA GTGGGGGCAG GCAGAAGGGA   2220

GAACCAGCTC AAGACATTTT GGAGGATCTG GCCCTGGGGT TCTTCAGAGA ACACCCTCTA   2280

GGGGCTTTGG GGACATGGCC TGTCCCCACA TCCAGCACTT GCCTCCGCCA TGGTCACTCG   2340

GCAGCCCTTT TCCCAGGAGA AGACACCTCT GGGAGCCTGC TCAGTGCTTG TCCTGCCATC   2400

CTGTGTCCTG GGACTGAGGG TTACTCCAGT TGCTCTGTGT TGCATACTCT CCCCCGCAAG   2460

CCTGTGTATG AAGAATTGTC CCCTGGCTTC AGCAGGCCA TGGCTGGCTG TTTTGTGACT   2520

GTTACATTGT GCAGGGGTAA TTATTAGCGT GGCTTTTACA CTTAAAAAAA AAA          2573
```

(2) INFORMATION FOR SEQ ID NO:3:

(i) SEQUENCE CHARACTERISTICS:
        (A) LENGTH: 329 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1399101

(xi) SEQUENCE DESCRIPTION: SEQ ID NO:3:

```
Ala Gly Leu Phe Gly Tyr Trp Gly Asn Lys Gly Val Asn Ile Cys
 1               5                  10                  15

Leu Lys Leu Tyr Gly Tyr Val Ser Ile Ile Asn Cys His Leu Pro
            20                  25                  30

Pro His Ile Ser Asn Asn Tyr Gln Arg Leu Glu His Phe Asp Arg Ile
        35                  40                  45

Leu Glu Met Gln Asn Cys Glu Gly Arg Asp Ile Pro Asn Ile Leu Asp
    50                  55                  60

His Asp Leu Ile Ile Trp Phe Gly Asp Met Asn Phe Arg Ile Glu Asp
65                  70                  75                  80

Phe Gly Leu His Phe Val Arg Glu Ser Ile Lys Asn Arg Cys Tyr Gly
                85                  90                  95

Gly Leu Trp Glu Lys Asp Gln Leu Ser Ile Ala Lys Lys His Asp Pro
            100                 105                 110

Leu Leu Arg Glu Phe Gln Glu Gly Arg Leu Leu Phe Pro Pro Thr Tyr
        115                 120                 125

Lys Phe Asp Arg Asn Ser Asn Asp Tyr Asp Thr Ser Glu Lys Lys Arg
    130                 135                 140
```

-continued

```
Lys Pro Ala Trp Thr Asp Arg Ile Leu Trp Arg Leu Lys Arg Gln Pro
145                 150                 155                 160

Cys Ala Gly Pro Asp Thr Pro Ile Pro Pro Ala Ser His Phe Ser Leu
                165                 170                 175

Ser Leu Arg Gly Tyr Ser Ser His Met Thr Tyr Gly Ile Ser Asp His
                180                 185                 190

Lys Pro Val Ser Gly Thr Phe Asp Leu Glu Leu Lys Pro Leu Val Ser
                195                 200                 205

Ala Pro Leu Ile Val Leu Met Pro Glu Asp Leu Trp Thr Val Glu Asn
210                 215                 220

Asp Met Met Val Ser Tyr Ser Ser Thr Ser Asp Phe Pro Ser Ser Pro
225                 230                 235                 240

Trp Asp Trp Ile Gly Leu Tyr Lys Val Gly Leu Arg Asp Val Asn Asp
                245                 250                 255

Tyr Val Ser Tyr Ala Trp Val Gly Asp Ser Lys Val Ser Cys Ser Asp
                260                 265                 270

Asn Leu Asn Gln Val Tyr Ile Asp Ile Ser Asn Ile Pro Thr Thr Glu
                275                 280                 285

Asp Glu Phe Leu Leu Cys Tyr Tyr Arg Asn Ser Leu Arg Ser Val Val
290                 295                 300

Gly Ile Arg Arg Pro Phe Gln Ile Pro Pro Gly Ser Leu Arg Glu Asp
305                 310                 315                 320

Pro Leu Gly Glu Ala Gln Pro Gln Ile
                325
```

(2) INFORMATION FOR SEQ ID NO:4:

(i) SEQUENCE CHARACTERISTICS:
        (A) LENGTH: 942 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1019103

(xi) SEQUENCE DESCRIPTION: SEQ ID NO:4:

```
Val Thr Val Pro Glu Pro Gly Ala Ala Glu Ser Arg Ala Pro Cys Gly
1               5                   10                  15

Asp Ser Ser Gly Gly Cys Val Arg Ser Ala Gly Ala Ser Met Asp Gln
                20                  25                  30

Ser Val Ala Ile Gln Glu Thr Leu Ala Glu Gly Glu Tyr Cys Val Ile
                35                  40                  45

Ala Val Gln Gly Val Leu Cys Glu Gly Asp Ser Arg Gln Ser Arg Leu
50                  55                  60

Leu Gly Leu Val Arg Tyr Arg Leu Glu His Gly Gly Gln Glu His Ala
65                  70                  75                  80

Leu Phe Leu Tyr Thr His Arg Arg Met Ala Ile Thr Gly Asp Asp Val
                85                  90                  95

Ser Leu Asp Gln Ile Val Pro Val Ser Arg Asp Phe Thr Leu Glu Glu
                100                 105                 110

Val Ser Pro Asp Gly Glu Leu Tyr Ile Leu Gly Ser Asp Val Thr Val
                115                 120                 125

Gln Leu Asp Thr Ala Glu Leu Ser Leu Val Phe Gln Leu Pro Phe Gly
                130                 135                 140

Ser Gln Thr Arg Met Phe Leu His Glu Val Ala Arg Ala Cys Pro Gly
```

-continued

```
            145                 150                 155                 160
        Phe Asp Ser Ala Thr Arg Asp Pro Glu Phe Leu Trp Leu Ser Arg Tyr
                        165                 170                 175
        Arg Cys Ala Glu Leu Glu Leu Glu Met Pro Thr Pro Arg Gly Cys Asn
                    180                 185                 190
        Ser Ala Leu Val Thr Trp Pro Gly Tyr Ala Thr Ile Gly Gly Gly Gly
                    195                 200                 205
        Ser Asn Phe Asp Gly Leu Arg Pro Asn Gly Lys Gly Val Pro Met Asp
            210                 215                 220
        Gln Ser Ser Arg Gly Gln Asp Lys Pro Glu Ser Leu Gln Pro Arg Gln
        225                 230                 235                 240
        Asn Lys Ser Lys Ser Glu Ile Thr Asp Met Val Arg Ser Ser Thr Ile
                        245                 250                 255
        Thr Val Ser Asp Lys Ala His Ile Leu Ser Met Gln Lys Phe Gly Leu
                    260                 265                 270
        Arg Asp Thr Ile Val Lys Ser His Leu Leu Gln Lys Glu Glu Asp Tyr
                    275                 280                 285
        Thr Tyr Ile Gln Asn Phe Arg Phe Phe Ala Gly Thr Tyr Asn Val Asn
                290                 295                 300
        Gly Gln Ser Pro Lys Glu Cys Leu Arg Leu Trp Leu Ser Asn Gly Ile
        305                 310                 315                 320
        Gln Ala Pro Asp Val Tyr Cys Val Gly Phe Gln Glu Leu Asp Leu Ser
                        325                 330                 335
        Lys Glu Ala Phe Phe His Asp Thr Pro Lys Glu Glu Trp Phe
                    340                 345                 350
        Lys Ala Val Ser Glu Gly Leu His Pro Asp Ala Lys Tyr Ala Lys Val
                    355                 360                 365
        Lys Leu Ile Arg Leu Val Gly Ile Met Leu Leu Leu Tyr Val Lys Gln
                370                 375                 380
        Glu His Ala Ala Tyr Ile Ser Glu Val Glu Ala Glu Thr Val Gly Thr
        385                 390                 395                 400
        Gly Ile Met Gly Arg Met Gly Asn Lys Gly Val Ala Ile Arg Phe
                        405                 410                 415
        Gln Phe His Asn Thr Ser Ile Cys Val Val Asn Ser His Leu Ala Ala
                    420                 425                 430
        His Ile Glu Glu Tyr Glu Arg Arg Asn Gln Asp Tyr Lys Asp Ile Cys
                    435                 440                 445
        Ser Arg Met Gln Phe Cys Gln Pro Asp Pro Ser Leu Pro Pro Leu Thr
            450                 455                 460
        Ile Ser Asn His Asp Val Ile Leu Trp Leu Gly Asp Leu Asn Tyr Arg
        465                 470                 475                 480
        Ile Glu Glu Leu Asp Val Glu Lys Val Lys Lys Leu Ile Glu Glu Lys
                        485                 490                 495
        Asp Phe Gln Met Leu Tyr Ala Tyr Asp Gln Leu Lys Ile Gln Val Ala
                    500                 505                 510
        Ala Lys Thr Val Phe Glu Gly Phe Thr Glu Gly Glu Leu Thr Phe Gln
                    515                 520                 525
        Pro Thr Tyr Lys Tyr Asp Thr Gly Ser Asp Asp Trp Asp Thr Ser Glu
                530                 535                 540
        Lys Cys Arg Ala Pro Ala Trp Cys Asp Arg Ile Leu Trp Lys Gly Lys
        545                 550                 555                 560
        Asn Ile Thr Gln Leu Ser Tyr Gln Ser His Met Ala Leu Lys Thr Ser
                        565                 570                 575
```

```
Asp His Lys Pro Val Ser Val Phe Asp Ile Gly Val Arg Val Val
            580             585             590

Asn Asp Glu Leu Tyr Arg Lys Thr Leu Glu Glu Ile Val Arg Ser Leu
            595             600             605

Asp Lys Met Glu Asn Ala Asn Ile Pro Ser Val Ser Leu Ser Lys Arg
            610             615             620

Glu Phe Cys Phe Gln Asn Val Lys Tyr Met Gln Leu Lys Val Glu Ser
625             630             635             640

Phe Thr Ile His Asn Gly Gln Val Pro Cys His Phe Glu Phe Ile Asn
            645             650             655

Lys Pro Asp Glu Glu Ser Tyr Cys Lys Gln Trp Leu Asn Ala Asn Pro
            660             665             670

Ser Arg Gly Phe Leu Leu Pro Asp Ser Asp Val Glu Ile Asp Leu Glu
            675             680             685

Leu Phe Val Asn Lys Thr Thr Ala Thr Lys Leu Asn Ser Gly Glu Asp
            690             695             700

Lys Ile Glu Asp Ile Leu Val Leu His Leu Asp Arg Gly Lys Asp Tyr
705             710             715             720

Phe Leu Ser Val Ser Gly Asn Tyr Leu Pro Ser Cys Phe Gly Ser Pro
            725             730             735

Ile His Thr Leu Cys Tyr Met Arg Glu Pro Ile Leu Asp Leu Pro Leu
            740             745             750

Glu Thr Ile Ser Glu Leu Thr Leu Met Pro Val Trp Thr Gly Asp Asp
            755             760             765

Gly Ser Gln Leu Asp Ser Pro Met Glu Ile Pro Lys Glu Leu Trp Met
770             775             780

Met Val Asp Tyr Leu Tyr Arg Asn Ala Val Gln Gln Glu Asp Leu Phe
785             790             795             800

Gln Gln Pro Gly Leu Arg Ser Glu Phe Glu His Ile Arg Asp Cys Leu
            805             810             815

Asp Thr Gly Met Ile Asp Asn Leu Ser Ala Ser Asn His Ser Val Ala
            820             825             830

Glu Ala Leu Leu Leu Phe Leu Glu Ser Leu Pro Glu Pro Val Ile Cys
            835             840             845

Tyr Ser Thr Tyr His Asn Cys Leu Glu Cys Ser Gly Asn Tyr Thr Ala
            850             855             860

Ser Lys Gln Val Ile Ser Thr Leu Pro Ile Phe His Lys Asn Val Phe
865             870             875             880

His Tyr Leu Met Ala Phe Leu Arg Glu Leu Leu Lys Asn Ser Ala Lys
            885             890             895

Asn His Leu Asp Glu Asn Ile Leu Ala Ser Ile Phe Gly Ser Leu Leu
            900             905             910

Leu Arg Asn Pro Ala Gly His Gln Lys Leu Asp Met Thr Glu Lys Lys
            915             920             925

Lys Ala Gln Glu Phe Ile His Gln Phe Leu Cys Asn Pro Leu
            930             935             940

(2) INFORMATION FOR SEQ ID NO:5:

(i) SEQUENCE CHARACTERISTICS:
        (A) LENGTH: 901 amino acids
        (B) TYPE: amino acid
        (C) STRANDEDNESS: single
        (D) TOPOLOGY: linear
```

-continued (vii) IMMEDIATE SOURCE:
    (A) LIBRARY: GenBank
    (B) CLONE: 1420920

(xi) SEQUENCE DESCRIPTION: SEQ ID NO:5:

```
Met Glu Pro Pro Leu Pro Val Gly Ala Gln Pro Leu Ala Thr Val Glu
 1               5                  10                  15

Gly Met Glu Met Lys Gly Pro Leu Arg Glu Pro Cys Ala Leu Thr Leu
                20                  25                  30

Ala Gln Arg Asn Gly Gln Tyr Glu Leu Ile Ile Gln Leu His Glu Lys
            35                  40                  45

Glu Gln His Val Gln Asp Ile Ile Pro Ile Asn Ser His Phe Arg Cys
        50                  55                  60

Val Gln Glu Ala Glu Glu Thr Leu Leu Ile Asp Ile Ala Ser Asn Ser
65                  70                  75                  80

Gly Cys Lys Ile Arg Val Gln Gly Asp Trp Ile Arg Glu Arg Arg Phe
                85                  90                  95

Glu Ile Pro Asp Glu Glu His Cys Leu Lys Phe Leu Ser Ala Val Leu
            100                 105                 110

Ala Ala Gln Lys Ala Gln Ser Gln Leu Leu Val Pro Glu Gln Lys Asp
        115                 120                 125

Ser Ser Ser Trp Tyr Gln Lys Leu Asp Thr Lys Asp Lys Pro Ser Val
130                 135                 140

Phe Ser Gly Leu Leu Gly Phe Glu Asp Asn Phe Ser Ser Met Asn Leu
145                 150                 155                 160

Asp Lys Lys Ile Asn Ser Gln Asn Gln Pro Thr Gly Ile His Arg Glu
                165                 170                 175

Pro Pro Pro Pro Phe Ser Val Asn Lys Met Leu Pro Arg Glu Lys
            180                 185                 190

Glu Ala Ser Asn Lys Glu Gln Pro Lys Val Thr Asn Thr Met Arg Lys
        195                 200                 205

Leu Phe Val Pro Asn Thr Gln Ser Gly Gln Arg Glu Gly Leu Ile Lys
    210                 215                 220

His Ile Leu Ala Lys Arg Glu Lys Glu Tyr Val Asn Ile Gln Thr Phe
225                 230                 235                 240

Arg Phe Phe Val Gly Thr Trp Asn Val Asn Gly Gln Ser Pro Asp Ser
                245                 250                 255

Gly Leu Glu Pro Trp Leu Asn Cys Asp Pro Asn Pro Pro Asp Ile Tyr
            260                 265                 270

Cys Ile Gly Phe Gln Glu Leu Asp Leu Ser Thr Glu Ala Phe Phe Tyr
        275                 280                 285

Phe Glu Ser Val Lys Glu Gln Glu Trp Ser Met Ala Val Glu Arg Gly
    290                 295                 300

Leu His Ser Lys Ala Lys Tyr Lys Lys Val Gln Leu Val Arg Leu Val
305                 310                 315                 320

Gly Met Met Leu Leu Ile Phe Ala Arg Lys Asp Gln Cys Arg Tyr Ile
                325                 330                 335

Arg Asp Ile Ala Thr Glu Thr Val Gly Thr Gly Ile Met Gly Lys Met
            340                 345                 350

Gly Asn Lys Gly Gly Val Ala Val Arg Phe Val Phe His Asn Thr Thr
        355                 360                 365

Phe Cys Ile Val Asn Ser His Leu Ala Ala His Val Glu Asp Phe Glu
    370                 375                 380

Arg Arg Asn Gln Asp Tyr Lys Asp Ile Cys Ala Arg Met Ser Phe Val
```

```
385                 390                 395                 400

Val Pro Asn Gln Thr Leu Pro Gln Leu Asn Ile Met Lys His Glu Val
                405                 410                 415

Val Ile Trp Leu Gly Asp Leu Asn Tyr Arg Leu Cys Met Pro Asp Ala
                420                 425                 430

Asn Glu Val Lys Ser Leu Ile Asn Lys Asp Leu Gln Arg Leu Leu
                435                 440                 445

Lys Phe Asp Gln Leu Asn Ile Gln Arg Thr Gln Lys Lys Ala Phe Val
    450                 455                 460

Asp Phe Asn Glu Gly Glu Ile Lys Phe Ile Pro Thr Tyr Lys Tyr Asp
465                 470                 475                 480

Ser Lys Thr Asp Arg Trp Asp Ser Ser Gly Lys Cys Arg Val Pro Ala
                485                 490                 495

Trp Cys Asp Arg Ile Leu Trp Arg Gly Thr Asn Val Asn Gln Leu Asn
                500                 505                 510

Tyr Arg Ser His Met Glu Leu Lys Thr Ser Asp His Lys Pro Val Ser
                515                 520                 525

Ala Leu Phe His Ile Gly Val Lys Val Val Asp Glu Arg Arg Tyr Arg
    530                 535                 540

Lys Val Phe Glu Asp Ser Val Arg Ile Met Asp Arg Met Glu Asn Asp
545                 550                 555                 560

Phe Leu Pro Ser Leu Glu Leu Ser Arg Arg Glu Phe Val Phe Glu Asn
                565                 570                 575

Val Lys Phe Arg Gln Leu Gln Lys Gly Lys Phe Gln Ile Ser Asn Asn
                580                 585                 590

Gly Gln Val Pro Cys His Phe Ser Phe Ile Pro Lys Leu Asn Asp Ser
                595                 600                 605

Gln Tyr Cys Lys Pro Trp Leu Arg Ala Glu Pro Phe Glu Gly Tyr Leu
    610                 615                 620

Glu Pro Asn Glu Thr Val Asp Ile Ser Leu Asp Val Tyr Val Ser Lys
625                 630                 635                 640

Asp Ser Val Thr Ile Leu Asn Ser Gly Glu Asp Lys Ile Glu Asp Ile
                645                 650                 655

Leu Val Leu His Leu Asp Arg Gly Lys Asp Tyr Phe Leu Thr Ile Ser
                660                 665                 670

Gly Asn Tyr Leu Pro Ser Cys Phe Gly Thr Ser Leu Glu Ala Leu Cys
                675                 680                 685

Arg Met Lys Arg Pro Ile Arg Glu Val Pro Val Thr Lys Leu Ile Asp
    690                 695                 700

Leu Glu Glu Asp Ser Phe Leu Glu Lys Glu Lys Ser Leu Leu Gln Met
705                 710                 715                 720

Val Pro Leu Asp Glu Gly Ala Ser Glu Arg Pro Leu Gln Val Pro Lys
                725                 730                 735

Glu Ile Trp Leu Leu Val Asp His Leu Phe Lys Tyr Ala Cys His Gln
                740                 745                 750

Glu Asp Leu Phe Gln Thr Pro Gly Met Gln Glu Glu Leu Gln Gln Ile
                755                 760                 765

Ile Asp Cys Leu Asp Thr Ser Ile Pro Glu Thr Ile Pro Gly Ser Asn
    770                 775                 780

His Ser Val Ala Glu Ala Leu Leu Ile Phe Leu Glu Ala Leu Pro Glu
785                 790                 795                 800

Pro Val Ile Cys Tyr Glu Leu Tyr Gln Arg Cys Leu Asp Ser Ala Tyr
                805                 810                 815
```

```
Asp Pro Arg Ile Cys Arg Gln Val Ile Ser Gln Leu Pro Arg Cys His
            820             825                 830

Arg Asn Val Phe Arg Tyr Leu Met Ala Phe Leu Arg Glu Leu Leu Lys
        835                 840                 845

Phe Ser Glu Tyr Asn Ser Val Asn Ala Asn Met Ile Ala Thr Leu Phe
        850             855                 860

Thr Ser Leu Leu Leu Arg Pro Pro Asn Leu Met Ala Arg Gln Thr
865                 870             875                 880

Pro Ser Asp Arg Gln Arg Ala Ile Gln Phe Leu Leu Gly Phe Leu Leu
            885             890                 895

Gly Ser Glu Glu Asp
            900
```